United States Patent [19]
Humpel et al.

[11] Patent Number: 5,124,267
[45] Date of Patent: Jun. 23, 1992

[54] METHOD FOR THE DETERMINATION OF SMALL SUBSTANCE QUANTITES OF MEDICINES, OF ENDOGENOUS OR OTHER CHEMICAL COMPOUNDS IN BIOLOGICAL MATERIAL

[75] Inventors: Michael Humpel; Werner Krause; Paul-Eberhard Schulze; Bob Nieuweboer, all of Berlin, Fed. Rep. of Germany

[73] Assignee: Schering Aktiengesellschaft, Berlin and Bergkamen, Fed. Rep. of Germany

[21] Appl. No.: 833,409

[22] Filed: Jan. 10, 1986

[30] Foreign Application Priority Data

May 10, 1984 [DE] Fed. Rep. of Germany ....... 3417638

[51] Int. Cl.⁵ .......................................... G01N 33/543
[52] U.S. Cl. ..................... 436/518; 250/282; 436/161; 436/173; 436/817
[58] Field of Search ............... 436/518, 161, 536, 538, 436/173, 817; 250/282

[56] References Cited

U.S. PATENT DOCUMENTS

| | | | |
|---|---|---|---|
| 4,022,876 | 5/1977 | Anbar | 436/542 |
| 4,134,792 | 1/1979 | Boguslaski et al. | 435/7 |
| 4,438,207 | 3/1984 | Fahrenholtz | 436/543 |
| 4,859,611 | 8/1989 | Groopman et al. | 436/824 X |

FOREIGN PATENT DOCUMENTS 495838 10/1974 Australia .

OTHER PUBLICATIONS

Wu, S., et al., Chem. Abstr. 100 (1984) #46441f.
Brumley, W. et al., Anal. Chem. 53:2003-2006 (1981).
Fischer S. et al., Biochem Biophys. Acta 710:493-501 (1982).
McBride, J. et al., Clin. Chem. 27(4):612-614 (1981).
Zamecnik, J. et al., Clin Chem. 24(4):627-630 (1978).
Tserng, K. Y. et al., Journ Chromatog. 272:233-241 (1983).
Chemical Abstracts, vol. 102:179213w.
Chemical Abstracts, vol. 96:174553e.

*Primary Examiner*—David Saunders
*Attorney, Agent, or Firm*—Millen, White & Zelano

[57] ABSTRACT

The invention relates to a process for the determination of small substance quantities of medicines, of endogenous or other chemical compounds in biological material, characterized by either binding the compound to be determined and its deuterated analog to an antibody present in excess, which antibody is coupled to a stationary phase of a polymeric material, and separating the two compounds from the antibody and measuring by mass spectrometry the proportion of deuterated compound/not deuterated compound or, respectively, cross-reacting compound; or, in case a suitable deuterated or cross-reacting compound is not available, utilizing as the internal standard also a chemically similar compound which, however, is added after the antibody-mediated extraction, and inserting a separating process before mass spectrometry.

9 Claims, 2 Drawing Sheets

METHOD FOR THE DETERMINATION OF SMALL SUBSTANCE QUANTITES OF MEDICINES, OF ENDOGENOUS OR OTHER CHEMICAL COMPOUNDS IN BIOLOGICAL MATERIAL

Radioimmunoassay (RIA) has been utilized for years as a sensitive method for determining minute quantities of endogenous substances or of medical agents. This method has heretofore been unsurpassed on account of the very sensitive physical detection ability of the radioisotopes employed for this purpose, such as, for example, $^{131}$iodine, $^{125}$iodine, tritium, and others. This test does display disadvantages in all those cases where metabolic products are concomitantly determined due to cross reactions during the determination of endogenous substances or foreign substances introduced by medicaments, and therefore information about the actual content of the compounds to be determined is difficult to obtain or even impossible to obtain. These cross reactions can never be excluded, in principle. They are dependent, in the final analysis, on the selectivity of the antiserum employed. In many cases, the metabolites from introduced medicines, evolving in the plasma, are unknown; as a consequence, testing of the antibody serum for specificity is impossible.

Besides this insecurity in specificity, the use of radioactive material also evokes additional problems in handling of the RIA method. Accommodations must be provided which are permitted by the authorities and are suitable for handling of the radioactive substances without danger. Therefore, efforts have been made for some time to find a determination method feasible without a radioactive tracer, devoid of a possible cross reaction, and wherein the specificity cf RIA is additionally increased.

J. of Chromatography 223 (1981): 193 describes use of a 17β-estradiol antiserum, bound in a covalent fashion to sepharose, for the extraction of 17β-estradiol from biological material. However, the determination method still utilizes tritium-labeled compounds.

It has now been found that minute quantities of matter from medicinal agents or from endogenous substances can be analyzed even without the corresponding radioactive tracers and with constant specificity of the antibody if the antibody is chemically coupled to a stationary phase, and a deuterated analog of the compound to be detected is employed. Determination takes place with the aid of gas chromatography coupled with mass spectrometry. The specificity of this novel analytical method is markedly raised as compared with the conventional RIA method.

While, in the RIA, the compound to be analyzed competes with the radioactive tracer during in vitro determination for the antibody, and thus must be added in a highly specific fashion, the novel method provides that the deuterated tracer is added to the biological sample and is separated quantitatively by way of a suitable stationary phase containing the antibody in excess. In this procedure, the not deuterated compound to be measured, present in the biological material, as well as the deuterated tracer are retained quantitatively by the antibody. It makes no difference for the subsequent analysis whether the antibody is additionally capable of binding still further compounds (cross reaction). The subsequent measurement has as its important factor merely the proportion of the not deuterated compound to be determined/deuterated compound. After the plasma has passed the stationary phase (with the antibody), a rewashing step is repeatedly carried out with a suitable washing liquid (in most cases with a solvent on which the phase is based, with the additives customary in biochemistry, chemistry, namely $NaHCO_3$, acetic acid, and buffers known to those in the art), such as, for example isotonic sodium chloride solution or water. Subsequently, the deuterated compound and the not deuterated compound are removed from the stationary phase and the proportion of the two compounds is determined by means of a mass spectrometer.

The method of this invention has the advantage over the conventional methods that (1) determination can be carried out without radioactivity, (2) possible cross reactions of the antibody with third substances (metabolites) are of no consequence, (3) its specificity exceeds that of RIA, and (4) the coupled antibody can be utilized repeatedly. With 50 extractions, no decompositions whatever could be observed.

Preferably, polymeric substrate materials are used as the stationary phase, such as, for example, sepharose, cellulose, "Carbopol", silica gel, etc. However, also suitable as the substrate material is $Al_2O_3$ (. x $H_2O$). The quantities of antibody usually employed amount to 50 μg to 1 mg. A further advantage of the novel method resides in its economy. While the known RIA method works with radioisotopes, the use of which is always accompanied by an incomparably high expense due to the special protective measures, the deuterated compounds required for the novel method can be prepared without any special protective steps, and their use in the novel method is consequently entirely without problems. Measurement in a mass spectrometer has, in the meantime, evolved into being part of the daily routine of a well-skilled laboratory personnel and thus requires no detailed explanation, since in this method it is merely necessary to place the recovered, not deuterated compound into direct relationship with the compound to be determined.

The novel method is suited for all compounds for which an antibody exists, namely for endogenous compounds, such as natural prostaglandins or steroid hormones, as well as for compounds foreign to the body, such as, for example, medicines or noxious chemicals.

Suitable tracers are not only deuterated compounds, but also the substances that can be labeled with stable isotopes, such as $^{13}C$, $^{15}N$, $^{18}O$, or similar isotopes.

Any polymeric matrix to which the antibody can be coupled can be utilized as the stationary substrate material.

In place of GC/MS, any other procedure can also be employed that can be used for determining the proportion of not deuterated compound/deuterated compound. Among these are, for example, MS by itself or MS-MS.

If a compound labeled with stable isotopes is unavailable, then it is also possible to utilize another, chemically similar compound. However, a prerequisite here is that it enters into a cross reaction with the antibody. In this case, extraction with the coupled antibody must be followed by another separating procedure, such as, for example, GC or HPLC, before the two compounds can be analyzed.

If neither an isotope-labeled nor a cross-reacting compound is available, it is also possible to employ another, chemically similar substance which in this case is added to the extract only after the antibody-mediated extraction. In case of iloprost, this was tested with carbacyclin.

For GC/MS measurement, the two masses m/z 493 and m/z 503 were then determined. All other conditions remained unchanged. The variation coefficient changes slightly in this case to 2.6% (n=5) with 50 pg samples.

Accordingly, the invention relates to a process for the determination of small substance quantities of medicines, of endogenous of other chemical compounds in biological material, characterized by either binding the compound to be determined and its deuterated analog to an antibody present in excess, which antibody is coupled to a stationary phase of a polymeric material, and separating the two compounds from the antibody and measuring by mass spectrometry the proportion of deuterated compound/not deuterated compound or, respectively, cross-reacting compound; or, in case a suitable deuterated or cross-reacting compound is not available, utilizing as the internal standard also a chemically similar compound which, however, is added after the antibody-mediated extraction, and inserting a separating process before mass spectrometry.

EXAMPLE 1

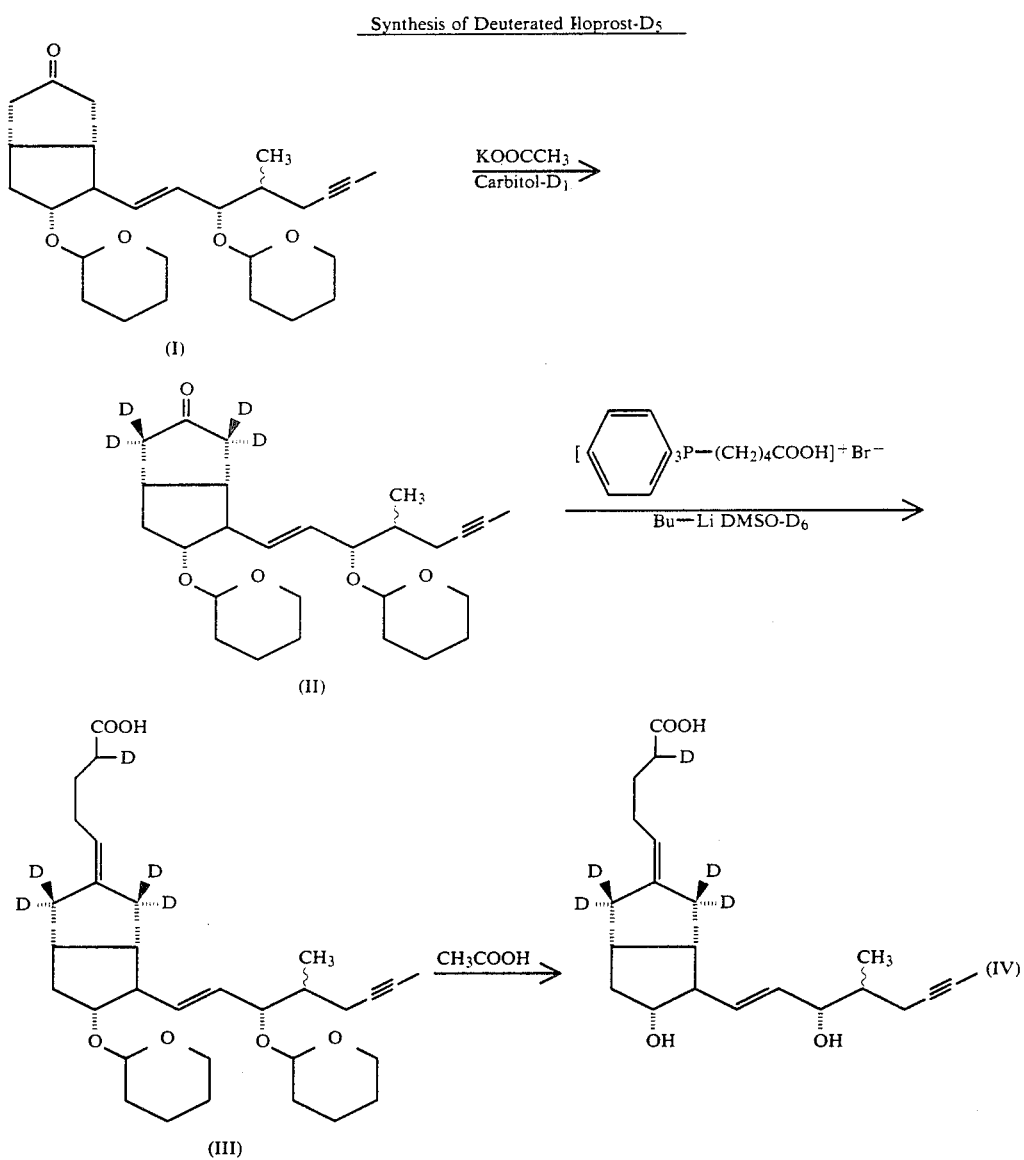

Figure 1:
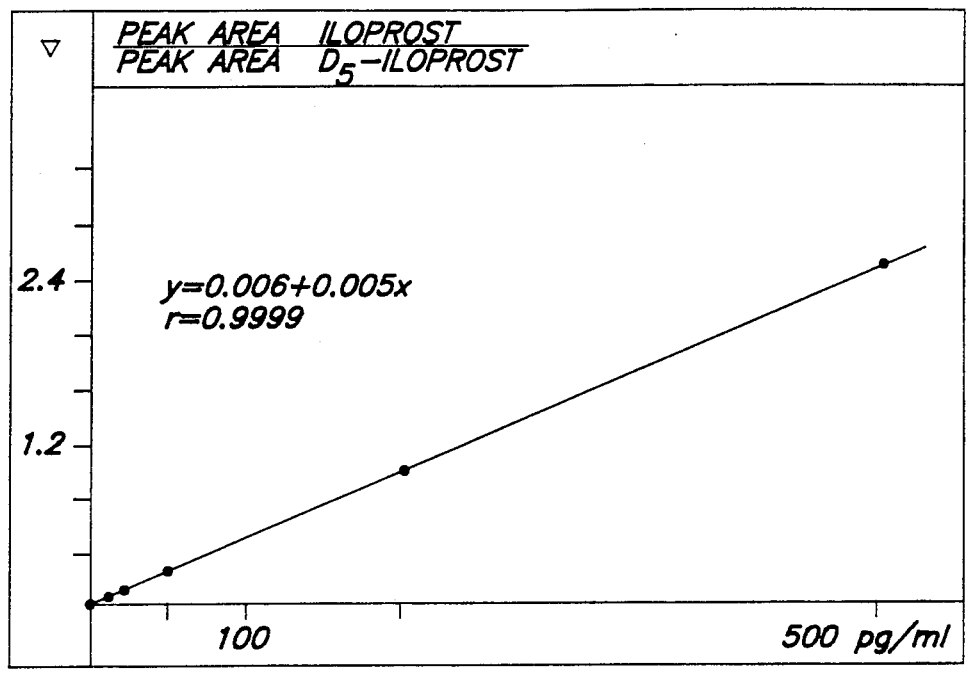
FIG. 1 shows a calibration line for iloprost determinations.

One gram (0.024 mmol) of compound I was added to a solution of 4.87 g (50 mmol) of anhydrous acetate in 130 ml (1.37 mol) of "Carbitol-$D_1$" while passing dry nitrogen through the reaction solution. The latter was stirred at room temperature until the compound was dissolved. Subsequently the solution remained standing for 21 days at room temperature, sealed and protected from light. For working-up purposes, 46 ml was withdrawn, combined with 30 ml of $D_2O$, and extracted three times with respectively 50 ml of dry hexane. The hexane phases were combined, washed twice with respectively 50 ml of $D_2O$, dried over sodium sulfate, and concentrated. The crude yield was 300 mg.

The thus-obtained compound II showed the following distribution of deuterium in the mass spectrum:

| | |
|---|---|
| $D_0$ | 3.3% |
| $D_1$ | 3.6% |
| $D_2$ | 11.2% |
| $D_3$ | 22.6% |
| $D_4$ | 52.6% |
| $D_5$ | 6.6% |

4.41 g (9.95 mmol) of 4-carboxybutyltriphenylphosphonium bromide was dissolved in 9.12 ml of dimethyl sulfoxide-$D_6$ and 4.62 ml of tetrahydrofuran dried over $Al_2O_3$, while passing nitrogen over the reaction solution. At 0°–8° C., 2.2 g (19.9 mmol) of potassium tert-butylate was added thereto under agitation.

After 30 minutes of stirring, 4.62 ml of this solution was added to compound II, dissolved in 1 ml of tetrahydrofuran (dried over $Al_2O_3$), and, under a stream of nitrogen gas, the mixture was stirred for 2 hours at 30° C. and subsequently overnight at room temperature. The progress of the reaction was tested by means of thin-layer chromatography in the system of ethyl acetate/hexane (3:2).

The solution was then combined with 25 ml of 30% citric acid and 50 ml of water and extracted exhaustively with methylene chloride. After drying with sodium sulfate, the mixture was concentrated, and the oily residue was purified via a low-pressure column on silica gel. The eluent was toluene/ethyl acetate in a gradient system (100:0 to 70:30). The yield of pure cis compound (III) was 105 mg.

Compound III was dissolved in 2 ml of tetrahydrofuran, combined with 3 ml of water and 3 ml of glacial acetic acid, and agitated for 24 hours at room temperature. After concentration under vacuum, the residue was dissolved in 2 ml of methylene chloride/isopropanol (9:1) and purified by way of a low-pressure column (10 g of silica gel, gradient methylene chloride/isopropanol, 9:1 to 7:3, respectively 2 hours, 80 ml/h). The yield of 5-[(E)-(1S,5S,6R,7R)-7-hydroxy-6-[(E)-(3S,4RS)-3-hydroxy-4-methyloct-1-en-6-ynyl]-[2-D,2-D,4-D,4-D]-bicyclo[3.3.0]octan-3-ylidene]-[2-D]-pentanoic acid (IV) was 20 mg.

Analytic procedure and confirmation of structure
Mass spectrum:

| | |
|---|---|
| $D_0$ | 2.8% |
| $D_1$ | 2.7% |
| $D_2$ | 7.3% |
| $D_3$ | 14.1% |
| $D_4$ | 29.2% |
| $D_5$ | 30.5% |
| $D_6$ | 3.1% |
| $D_7$ | 3.6% |
| $D_8$ | 2.0% |
| $D_9$ | 2.7% |
| $D_{10}$ | 2.1% |

HPLC: "Lichrosorb RP-18", 5 μm. 250 × 4.6 mm Methanol/water/glacial acetic acid, 70:30:0.6, 1.5 ml/min UV detection at 205 nm
TLC: Silica gel Methylene chloride/isopropanol (9:1), ethyl acetate (100)
Co-chromatography with conventional comparative material yielded complete identity.

EXAMPLE 2

Coupling of Antibody to Stationary Phase 22 mg of the antibody for iloprost described in Prostagland. Leukotr. Med. 10:289 (1983) was coupled to 2.4 g of CNBr-activated sepharose 4B (Pharmacia). For this purpose, the sepharose was first washed with 500 ml of $10^{-3}$-molar hydrochloric acid. Subsequently, the antibody was added in 0.1-molar $NaHCO_3$ solution (+0.5-molar NaCl). After 2 hours of rotating, the reaction mixture was washed with 0.1-molar acetate buffer (pH 4, with addition of 1-molar NaCl) and thereafter with 0.1-molar borate buffer (pH 8, 1-molar NaCl). Excess active groups were deactivated with 1-molar ethanolamine. The mixture was then washed two more times with acetate buffer and, respectively, borate buffer. The antibody coupled to sepharose was stored in 25 ml of 0.1-molar phosphate buffer (pH 7) at 4° C. with exclusion of light).

EXAMPLE 3

Extraction of Iloprost from Biological Material 0.88 mg of the sepharose-coupled antibody (corresponding to 1 ml of phosphate buffer) is introduced into a Pasteur pipette secured against leakage by a plug of cotton wool and washed with water, acetone, and again water. Subsequently, the biological phase, e.g. plasma, is combined with 300 pg of $D_5$-iloprost, introduced into the Pasteur pipette, and washed again with 10 ml of water. The volume of the sample is without significance, as could be demonstrated for up to 20 ml of plasma. After the washing step, the gel is blow-dried with air and deuterated and not deuterated iloprost is eluted with 10 ml of acetone/water (95:5, v/v). After the first 5 ml has passed through, the Pasteur pipette is sealed for one hour. The resultant extracts are combined and concentrated to dryness under vacuum. The residue is derivatized for GC/MS analysis.

The extraction yield with the use of the stationary antibody was >90% and was independent of the iloprost concentration.

| Extraction Yield from 1 ml of Plasma with the Use of Tritium-Labeled Iloprost (n = 5): | |
|---|---|
| Concentration (pg/ml) | Extraction Yield (%) |
| 10 | 91 ± 2 |
| 100 | 91 ± 2 |
| 1000 | 93 ± 1 |

EXAMPLE 4

Derivatization

The residue is taken up in 100 μl of acetonitrile (with 5% methanol) and combined with 10 μl of a solution of pentafluorobenzyl bromide (30% in acetonitrile, w/v) and 10 μl of N-ethylbisisopropylamine. After 40 minutes at 40° C., the solution is concentrated to dryness with a nitrogen stream and combined with 10 μl of BSTFA. After 30 minutes at 50° C., the sample is ready for GC/MS analysis.

EXAMPLE 5

GC/MS Analysis

For measuring the proportion of not deuterated iloprost/deuterated iloprost, a GC/MS instrument of the Finnigan 4021 type was utilized. This device contained the following modules: GC (type 9610), MS (type 4000) with PPNICI unit, INCOS 2100 data system. The separation by gas chromatography was conducted with the use of a CP-Sil 5 CB quartz capillary column (25 m ID 0.23 mm, film density 0.12 μm, company: Chrompack), introduced directly into the mass spectrometer. The carrier gas was helium with an inlet pressure of 24 psi. The samples were injected without split at 280° C. The temperature program of the column began at 150° C. (1 min) and reached 310° C. with a heating rate of 20° C./min. The mass spectrometer was operated at a temperature of 240° C. The electron energy was 70 eV, and the emission current was 0.2 μA. The secondary electron multiplier was set at 1.5 kV, the preamplifier at $10^{-8}$ A/V. Iloprost and $D_5$-iloprost were determined with NC I (negative ions—chemical ionization) and individual ion detection (MID) at m/z 503 and 508, respectively.

EXAMPLE 6

Evaluation

Evaluation of measured data takes place by comparison of the peak area ratios of iloprost/$D_5$-iloprost with a calibration line. The calibration line is obtained by extraction of samples of known concentration and plotting the peak area ratio of iloprost/$D_5$-iloprost against the concentration: See FIG. 1.

EXAMPLE 7

The higher specificity of the novel method as compared with the radioimmunoassay can be derived from the table below. In spite of the use of the same antibody, the concentrations measured with the novel method were markedly lower than those determined by means of RIA. This applies, above all, to the later points in time after application, where predominantly (cross-reacting) metabolites are to be expected in the plasma.

Comparison of the iloprost concentrations measured by RIA and, respectively, by the novel method, in 5 test volunteers. Administration was by intravenous infusion of 1 or of 3 ng/kg/min over 45 minutes, or an oral dose of 1 μg/kg. The plasma samples from, respectively, an early time zone (15–45 min and 0–15 min, respectively) and a late time zone (60–90 min and 50–90 min, respectively) were combined, and the iloprost concentration measured in these mixed samples.

| | | (pg/ml) | |
|---|---|---|---|
| | Sample | RIA | Novel Method |
| i.v. | (1 ng/kg/min; 45 min) 15–45 min | 59 | 35 |
| i.v. | (1 ng/kg/min; 45 min) 60–90 min | 24 | 4 |
| i.v. | (3 ng/kg/min; 45 min) 15–45 min | 146 | 152 |
| i.v. | (3 ng/kg/min; 45 min) 60–90 min | 49 | 13 |
| p.o. | (1 μg/kg) 0–15 min | 166 | 123 |
| p.o. | (1 μg/kg) 50–90 min | 99 | 20 |

EXAMPLE 8

Figure 2:
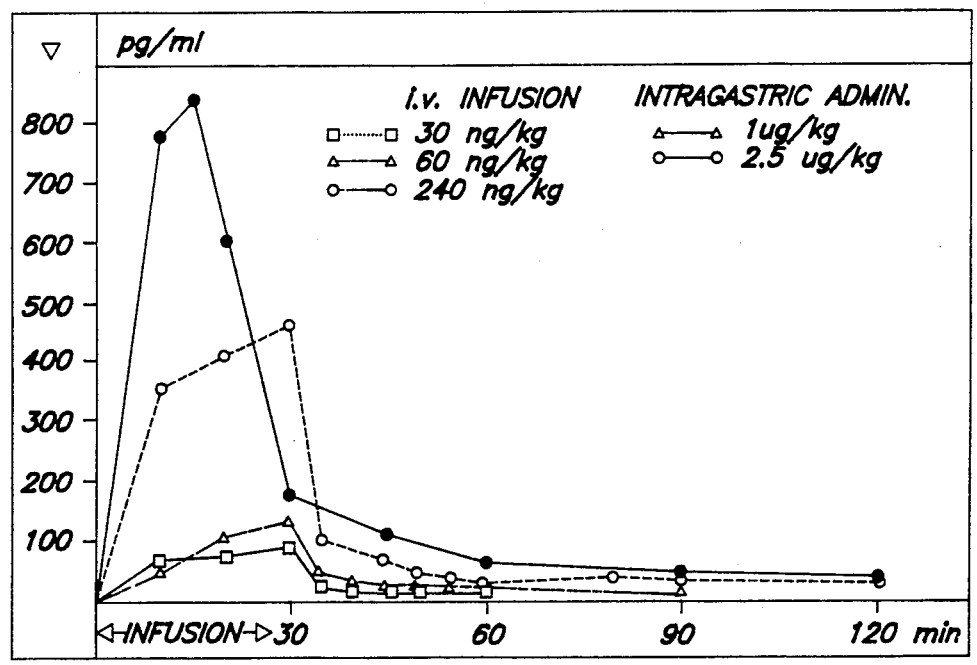
FIG. 2 shows plasma levels of iloprost as a function of time.

The figure below illustrates the plasma levels of iloprost determined with the aid of the antibody/GC/MS method. The iloprost plasma levels of 5 male test persons are depicted, obtained by administration of either a 30 minute intravenous infusion of 1, 2 or 8 ng/kg/min, or an intragastric dose of 1 or 2.5 μg/kg. See FIG. 2.

EXAMPLE 9

Carbacyclin can also be utilized as an internal standard in place of iloprost-$D_5$. In this case, the standard must be added after extraction. In place of m/z 508, m/z 493 is determined in the mass spectrometer. Reproducibility differs only to a minor extend from that with deuterated iloprost, as can be seen from the numerical comparison set forth below:

| Carbacyclin: | 2.6% | 50 pg/5 ml | n = 5 |
|---|---|---|---|
| Deuterated iloprost: | 2.3% | 50 pg/ml | n = 5 |
| | 1.1% | 100 pg/ml | n = 5 |

Figure 3:
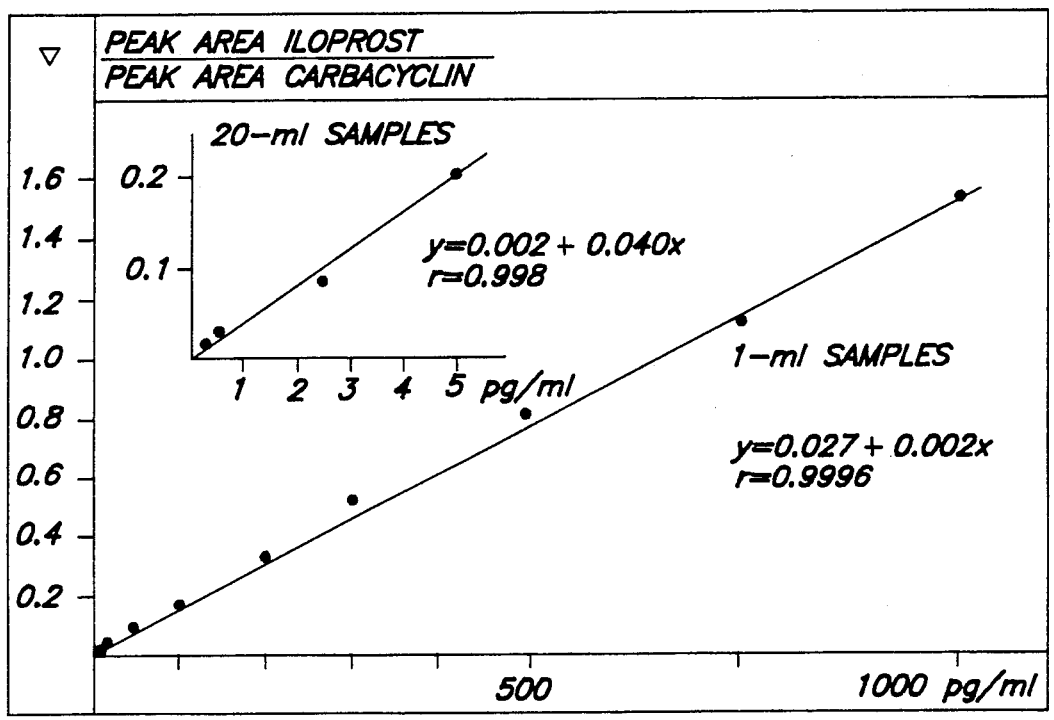
FIG. 3 shows a comparison of iloprost and carbacyclin determinations by two different methods of this invention.

See FIG. 3.

The variation coefficient was 2.3% with a concentration of 50 pg/ml and 1.1% with 100 pg/ml (respectively n=5). The detection limit was about 5 pg/ml with the use of 1 ml of plasma and 0.25 pg/ml with the use of 20 ml of plasma. The detection limit calculated for radioimmunoassay with the same antibody amounted to 20 pg/ml.

EXAMPLE 10

Estradiol was analyzed in correspondence with the examples recited above.

EXAMPLE 11

11-Nor-9-tetrahydrocannabinol-9-carboxylic acid (primary THC metabolite) was determined in correspondence with the aforedescribed examples.

We claim:

1. A method for determining a small amount of a chemical compound in a sample, comprising adding to the sample a known amount of a stable isotopic analog of said compound, binding said analog and said compound to an excess of antibody on a stationary phase for both said analog and compound, releasing said analog and compound from the antibody, and determining by mass spectrometric analysis the ratio of the released amount of said isotopic analogue to the released amount of said chemical compound wherefrom the amount of said chemical compound is calculable.

2. A method of claim 1, wherein said isotopic analog is a deuterated analog of said chemical compound.

3. A method of claim 1, wherein said antibody is bound to a stationary phase.

4. A method of claim 3, wherein, prior to said mass spectrometry step, said isotopic analog and chemical compound are separated from each other by gas chromatography.

5. A method of claim 1, wherein said chemical compound is a medicinal substance or an endogenous chemical substance in a biological sample.

6. A method of claim 5, wherein said medicinal substance is Iloprost, estradiol or 11-Nor-9-tetrahydrocannabinol-9-carboxylic acid.

7. A method for determining a small amount of a compound in a sample, comprising adding to the sample a known amount of a compound which cross-reacts with an antibody to said chemical compound, binding said chemical compound and said cross-reacting compound to an excess of said antibody on a stationary phase, releasing said chemical and cross-reaction compound from the antibody, separating the chemical and cross-reacting compounds from each other, and determining by mass spectrometric analysis the ratio of the released amount of said cross-reacting compound to the released amount of said chemical compound wherefrom the amount of said chemical compound is calculable.

8. A method for determining a small amount of a chemical compound in a sample, comprising extracting said compound from said sample by binding said compound to an excess of antibody on a stationary phase therefor and separating said compound from said antibody, adding to said separated compound a known amount of a chemical analog of said compound, which is not merely a deuterated analog thereof, of sufficient structural similarity to provide an accurate standard for said compound, thereafter separating said analogous compound from said compound and analyzing each of said separated compounds by mass spectrometry in order to determine a ratio of the amount of said chemical compound to the amount of said added analogous compound, wherefrom the amount of said chemical compound is calculable.

9. A method for determining a small amount of a chemical compound in a sample, comprising determining by mass spectrometric analysis the ratio of the amount of a stable isotopic or cross-reacting analog of said compound in said sample to the amount of said chemical compound in said sample in order to correlate therewith a determination of the amount of said chemical compound, said stable isotopic or cross-reacting analog having been added to said sample in a known amount and both said stable isotopic or cross-reacting analog and said chemical compound having been separated from said sample by binding to an excess of antibody on a stationary phase for both said isotopic or cross-reacting analog and said chemical compound and thereafter having been released from the antibody prior to said ratio determination step, said cross-reacting analog being a compound which cross-reacts with said antibody.

* * * * *